(12) United States Patent
Shivkumar et al.

(10) Patent No.: US 12,297,357 B2
(45) Date of Patent: May 13, 2025

(54) TEMPERATURE-SENSITIVE INDICATOR

(71) Applicant: Thermographic Measurements Ltd, Devon (GB)

(72) Inventors: Bagavant Shivkumar, Merseyside (GB); Philippe Marrec, Lannion (FR)

(73) Assignee: Thermographic Measurements Ltd, Devon (GB)

( * ) Notice: Subject to any disclaimer, the term of this patent is extended or adjusted under 35 U.S.C. 154(b) by 85 days.

(21) Appl. No.: 17/576,263

(22) Filed: Jan. 14, 2022

(65) Prior Publication Data

US 2022/0135804 A1 May 5, 2022

Related U.S. Application Data

(63) Continuation of application No. 15/757,260, filed as application No. PCT/EP2016/001495 on Sep. 5, 2016, now Pat. No. 11,225,577.

(30) Foreign Application Priority Data

Sep. 3, 2015 (GB) .................................. 1515610

(51) Int. Cl.

| | |
|---|---|
| *C09D 11/00* | (2014.01) |
| *C07C 69/78* | (2006.01) |
| *C09B 57/00* | (2006.01) |
| *C09B 67/02* | (2006.01) |
| *C09D 5/26* | (2006.01) |
| *C09D 5/33* | (2006.01) |
| *C09D 11/037* | (2014.01) |
| *C09D 11/17* | (2014.01) |
| *C09D 11/50* | (2014.01) |
| *C09K 9/02* | (2006.01) |
| *G01N 21/78* | (2006.01) |

(52) U.S. Cl.
CPC .......... *C09B 67/0097* (2013.01); *C07C 69/78* (2013.01); *C09B 57/00* (2013.01); *C09D 5/004* (2013.01); *C09D 5/26* (2013.01); *C09D 11/037* (2013.01); *C09D 11/17* (2013.01); *C09D 11/50* (2013.01); *C09K 9/02* (2013.01); *G01N 21/78* (2013.01); *C09K 2211/1007* (2013.01)

(58) Field of Classification Search
CPC ... C09B 67/0097; C09B 57/00; C09D 11/037; C09D 11/17; C09D 11/50; G01N 21/78
USPC ................................ 106/31.01, 31.13, 31.32
See application file for complete search history.

(56) References Cited

U.S. PATENT DOCUMENTS

| | | | | |
|---|---|---|---|---|
| 11,225,577 B2 * | 1/2022 | Shivkumar | ............ | G01N 21/78 |
| 2016/0289508 A1 * | 10/2016 | Meincke | ................... | C09J 9/00 |

FOREIGN PATENT DOCUMENTS

WO    WO-2015074953 A1 *  5/2015    ........... C08K 5/0041

* cited by examiner

*Primary Examiner* — James E McDonough
(74) *Attorney, Agent, or Firm* — Cook Alex Ltd.

(57) ABSTRACT

A temperature-indicator product comprising a visual indicator comprising a thermochromic colour-memory composition and comprising an electron-donating colouring organic compound (A), an electron-accepting colouring organic compound (B) and reaction medium compound (C). The visual indicator comprises a first portion comprising a first thermochromic colour-change composition in its lower temperature state and a second portion comprising a second thermochromic colour-change composition in its higher temperature state. The product is useful as a tamper-evident indicator or as a freeze indicator.

9 Claims, 2 Drawing Sheets

TEMPERATURE-SENSITIVE INDICATOR

CROSS-REFERENCE TO RELATED APPLICATIONS

This is a Continuation Application of U.S. National Stage application Ser. No. 15/757,260, filed Mar. 2, 2018 which is a U.S. National Stage of International PCT Application No. PCT/EP2016/001495, filed Sep. 5, 2016 which claims the benefit of and priority to Great Britain Application No. 1515610.2, filed Sep. 3, 2015, the disclosures of which are hereby incorporated by reference in their entireties.

This invention relates to temperature-sensitive indicator and particularly to an article comprising a temperature-sensitive indicator, for example a label. The temperature-sensitive indicator provides a tamper-evident indicator and in another application provides a cold temperature or "freeze" indicator. The composition comprises a thermochromic composition or, a microencapsulated colour material, such as a pigment comprising the thermochromic composition.

Temperature-sensitive indicators are known and used in a wide range of applications including in packaging of individual and bulk products, for example in containers or on pallets to provide an indication of whether a product has been tampered with or whether it has been subjected to undesirable high or low temperatures for example through temperature cycling during storage or in the supply chain. Other fields of use include electronics, aerospace and automotive applications in which temperature control is critical to ensure the integrity of equipment, confirm that surface temperatures are achieved for curing-bonding, confirm that soldering temperatures have been achieved, confirm temperature integrity of machines, temperature recordal in plant, laboratory equipment and for electronic devices in in accessible locations. Indicating a minimum and/or maximum temperature to which products have been exposed is particularly important in relation to pharmaceutical products, chemicals, perishable products such as foodstuffs, for instance fruit and vegetables.

There are many fields of use in which it is important to ensure security of a product for example in transporting currency, documents, valuable goods and the like. Presently, systems exist for such secure transferal or transportation and to provide an indication that an article has been tampered with or subjected to unauthorised viewing or other fraud but there remains a need for improved security.

Problems of unauthorised secret access to sealed packages are especially prevalent and difficult to address. Sealed packages for example containing currency or confidential documents may be subjected to unauthorised and secret opening and resealing such that the intended recipient or the sender is not aware of interception of the package. This unauthorised opening may involve heating the adhesive to a temperature at which it softens and ceases to adhere the package thereby allowing access. The package may then be resealed. An alternative method involved freezing the adhesive such that it becomes brittle and ceases to act as an adhesive thereby affording access to the package. Heating the adhesive may then allow it to regain its adhesive properties such that the unauthorised access is not detectable.

Permanent colour change inks which change colour and remain in that changed state if heated to a certain temperature have been used as a component of the adhesive or applied, for example by printing, as a separate strip or application of the ink near to the adhesive such that if heat is applied, the ink changes colour permanently and thereby provides a visual indication of the attempted unauthorised entry. This method is not usable however when the freezing approach is employed.

A need to improve the security of sealed packages or articles in a cost effective and reliable manner remains.

For certain products it is essential to know whether the product has been subjected to a temperature below a certain level for reasons of health and safety and for quality assurance and the like. For example certain medical products such as vaccines must not be subjected to temperatures below around 2° C. or the efficacy of the vaccine may be compromised with adverse and potentially dangerous consequences for individual or public health.

Adhesives find wide-spread use in many fields in the manufacture of goods for example motor vehicles and in aerospace in which ensuring effective bonding between parts is essential for quality control and also for product safety. It is important to be aware of whether an adhesive has been subjected to temperature cycling or heated or cooled above or below a threshold temperature at which its function may be impaired, Certain indicators are used to indicate exposure to low temperatures of freezing temperatures and "freeze indicators" are known and comprise electronic means or chemical means of indicating a given temperature. Typically a visual indication for example a permanent colour change, upon exposure to a certain temperature.

Known freeze indicator products are relatively bulky items and are used for indicating the temperature of bulk-packaged goods, for example on pallets and in goods containers. The size or bulk of known temperature-indicators renders them unsuitable for use as indicators for smaller or individually packaged products. Furthermore, known products typically contain a liquid or a mixtures of liquids embedded in a pouch and their costs of manufacture are relatively high due to low speeds of processing.

Accordingly, there remains a need for tamper-evident security product and a temperature-indicator product which provides a visual record of a low temperature indication and/or a maximum temperature indication. A further need exists to provide a product which may exist in two different coloured states at a given temperature and which are economic to produce, suitable for labelling of individual products and are not bulky.

We have now found that a thermochromic composition may be used to provide a novel temperature-indicator product such as a label which provides an effective and reliable indication of unauthorised tampering or of being exposed to a pre-determined low temperature and which may be tailored to provide desired hysteresis characteristics and flexibility in formulating the colour-change composition.

The invention provides in a first aspect a temperature-indicator product comprising a visual indicator comprising a thermochromic colour-memory composition and comprising an electron-donating colouring organic compound (A), an electron-accepting colouring organic compound (B) and reaction medium compound (C).

The invention further provides a temperature-indicator product comprising a first portion of a thermochromic colour-change composition in its coloured state and a second portion of a thermochromic colour-change composition in its discoloured state wherein the composition comprises a reaction medium compound (C), preferably of formula (I) to (VII), an electron donating compound and an electron-accepting compound as described herein.

The thermochromic composition in the first portion and in the second portion may be the same or different. Suitably, the composition in the first area will be in its lower temperature state, typically coloured, and the composition in the second area will be in its higher temperature state, typically discoloured.

In a preferred embodiment, the same thermochromic composition is employed in the first portion and the second portion. If the indicator is subjected to a raised temperature above the colour change temperature of the first portion, both compositions will then exit in their higher temperature state. If the indicator is subjected to a lowered temperature below the colour change temperature of the second portion, both portions will then be in their lower temperature state. It will not be possible for the indicator to be placed in a state where the two portions are in respectively a lower and a higher temperature state and thereby provides evidence of exposure to temperature. Where an attempt is made to open a sealed package by freezing or heating the sealing adhesive to which the indicator is applied, the typical process of gaining unauthorised access will cause the indicator to change state irreversibly.

The temperature indicator is preferably a label.

In a preferred embodiment the product accordingly comprises a thermochromic composition which is able to exist in both a coloured state and in a discoloured state at a predetermined temperature.

Thermochromic compositions are known for use in writing implements and in toys and the like and change between a discoloured state and coloured state colour or between a first and second coloured state. Colour-change compositions may change colour upon the application of energy for example with a change in temperature or with a change in pressure. Colour-change compositions which change colour with a change in temperature are widely known as thermochromic compositions. Colour-change compositions may also be referred to as colour memory compositions.

In this specification, reference will be made to change between a discoloured and coloured state for convenience but this also encompasses a change between a first coloured state and a second coloured state. Colour-change compositions typically comprise an electron-donating colour-developing organic compound or leuco dye, an electron-accepting compound or colour developer and a compound acting as a reaction medium for reversible electron exchange between the electron-accepting and electron-donating compounds or colour change temperature regulator. The components of the composition are typically micronized or enclosed in microcapsules and may be formulated to produce an ink composition.

Thermochromic compositions reversibly change colour or change between a coloured and discoloured state when subjected to a change in temperature of a sufficient magnitude. Typically, an increase in temperature will lead to the ink having a discoloured state while cooling will lead to reappearance of colour. As temperature increases, the thermochromic composition will retain colour until the temperature reaches a maximum temperature for retention of the complete coloured state, known as the "maximum colour-retaining temperature" or $T_3$ as shown in FIG. 1 of the accompanying drawings. The composition will then become progressively discoloured as the temperature increases until it reaches a completely discoloured state at a temperature known as the "complete discolouring temperature" or $T_4$, the minimum temperature for achieving the completely discoloured state. The mean temperature between $T_3$ and $T_4$ is known as $T_G$.

As the thermochromic composition cools from a discoloured state, the composition remains discoloured until a temperature is reached below which colour reappears, known as the "minimum discoloured state retaining temperature) or $T_2$ as the temperature decreases, colour reappears fully at a temperature known as the "complete colouring temperature" or $T_1$. The mean temperature between $T_1$ and $T_2$ is referred to as $T_H$. The thermochromic composition has a hysteresis width, known as ΔH which is the temperature difference between $T_H$ and $T_G$.

As the composition is subject to heating or cooling, the coloured state or discoloured state of the thermochromic composition may be retained after removal of the source of heat or cold required for respectively discoloration or coloration. Depending on whether the composition approaches a particular temperature from a lower or higher temperature, the composition may be coloured or discoloured at that particular temperature.

Where the thermochromic composition is heated above a certain temperature, in the discoloured state, the coloured state may not reappear on cooling the composition until temperature $T_1$ is reached. This may be referred to as the "locking temperature" This provides a means of determining whether the composition has been subjected to the locking temperature which may be beneficial especially in medical applications or other applications where health or safety considerations are important. The hysteresis width, locking temperature and the minimum temperature at which colour reappears are dependent on the components of the composition.

The components of the composition may be selected to achieve a desired colour memory effect and hysteresis width and T4 temperature dependent on the intended use.

In a further embodiment, the product comprises two thermochromic colour memory compositions, the first composition and second composition having different locking temperatures.

In another embodiment, the product comprises a thermochromic colour memory composition and a permanent ink.

The permanent ink suitably has a colour change temperature below the colour change temperature of the thermochromic composition.

Known chemical temperature indicators typically contain a colour change composition comprising an electron donative colouring organic compound (A), an electron accepting colouring organic compound (B) to form the thermochromic and a reaction medium.

Compositions and pigments according to the invention provide a wide hysteresis and a tuneable hysteresis. By varying the colour-change composition formulation the width of the hysteresis may be varied and the complete decolouring temperature T4 may be varied, allowing excellent flexibility in the design of the colour-change microcapsule pigment.

Advantageously, the temperature-indicator product is in the form of a printable article or label and the thermochromic composition enables production of a label or article using known medium and high speed printing processes for example screen printing, flexographic printing, gravure printing process.

The use of medium or high speed printing allows a large volume of labels or articles to be produced and makes such products economically feasible for labelling individual products or packages as well as for larger packs, pallets or containers.

In a preferred embodiment, the temperature-sensitive product is a security label.

In one embodiment, the colour-change feature of the temperature-indicator product comprises and may consist of a thermochromic or printed memory composition as described herein. Advantageously, the composition is capable of being in 2 different coloured states at the same temperature.

In another embodiment the indicator may also be configured so it may not be reset and provides a single use indicator. Suitably, the thermochromic composition further comprises an ink which exhibits a permanent change of colour at a given temperature.

The invention provides for a single use temperature-indicator product comprising a first portion of a colour-change composition in its coloured state and a second portion of the same colour-change composition in its discoloured state wherein the composition comprises a reaction medium© as described below, preferably a compound of formula (I) to (VII) as described herein.

Suitably, the indicator has a thermochromic composition or pigment suitably in the form of a printable ink applied to it and heated to a temperature exceeding T4 prior to application to the indicator, for example in a printing process. An ink showing permanent colour change at a desired temperature, for example 50° C. is applied to the indicator, for example printed next to the memory composition pigment converted into printed ink. The composition is suitably selected such that T3 and T4 are higher than the transition temperature of the permanent colour change ink, for example 50° C.

Any known permanent colour change ink may be employed and a preferred example is available from TMC Hallcrest, under the brand name Kromagen. The printed label is allowed to dry at temperature not exceeding T3 or 50° C. and preferably not below $T_2$. The combination on the label is now suitable for indication of temperature below T2, for example 2° C. or 0° C. if the composition is selected such that T2 is 2° C. or 0° C. respectively, of what can be cold a "freeze indicator". The indicator is suitably used a single time and thereby provides an indication of the indicator having been subjected to a temperature below T2.

In another preferred embodiment, the thermochromic composition is printable and provides a memory function in that it provides an indication of a previous temperature to which the composition has been subjected.

Advantageously, temperature indicator products according to the invention for example labels, may be produced using medium to high speed printing process for example screen printing, flexographic printing and gravure printing which facilitates production of labels for use with individual packages as well as for larger packs, pallets or containers.

The thermochromic compositions described herein for use in the temperature-indicator product of the present invention may be employed in inks for multiple printing mode offset, flexo, gravure, screen, 3D printing, pad printing, spray coating and other coating modes and ink jet. The present memory colour-change composition or pigment can give memory colour change property to a variety of different substrates and materials suitable for use as temperature indicator products: gel, inks, paper, synthetic paper, coated paper, fiber, plastics, glass metal ceramic, wood, stone, plastics, concrete, synthetic glass.

Colour-change compositions as described herein are suitably useful in the production of printing inks for preparation of labels to provide a temperature indicator. Prior art with conventional colour-change compositions typically indicate when a particular temperature is reached without any further indication.

The colour-change composition or pigment suitably provides an indication of when temperature T4 is exceeded by remaining colourless, until the composition is subjected to temperature T1 and regaining colour at this point.

In a preferred embodiment, the colour-change composition or pigment where component C) is such that the composition or pigment temperature has a T2 temperature at a first temperature, for example 0° C. and a T3 temperature above a second temperature, for example 50° C.

A composition with these characteristics allows the design of an indicator which provides an indication of whether the indicator has been subjected to a particular temperature.

Suitably, the indicator is printed with a memory composition pigment, preferably converted into printed ink, heated to temperature exceeding temperature T4 prior to the printing process. A second sample of the composition is then suitably cooled to below temperature T1 and printed on the indicator, suitably next to the first print of the thermochromic composition. The printed label is allowed to dry at temperature not exceeding temperature T3 and not below temperature T2.

In a further aspect, the invention provides a process for producing an indicator comprising providing a support with a first portion of the colour-change composition, pigment or ink having colour change temperatures T1, T2, T3 and T4, heating the first portion of the colour-change composition, pigment or ink to a temperature exceeding T4, cooling a second portion of the colour-change composition, pigment or ink composition to a temperature below T1, applying the said second portion to the support and drying the colour-change composition, pigment or ink composition at temperature not exceeding temperature T3 and not below temperature T2.

The combination on the label is now suitable for indication of temperature below T2. By tuning the temperature T2 to 0° C., the indicator may be employed to provide a visual or readable indication of when the indicator and any article or material to which it is applied has been subjected to a temperature of less than 0° C. In this way, the indicator may act as a "freeze indicator".

The components A), B) and C) of the composition may be selected and the relative amounts employed to tailor properties of the composition to the desired use. The component is suitably selected to provide the desired practical hysteresis and the sensitivity of the colour change, as well as the temperature T1 and T4.

Suitably, the practical hysteresis range may be from 10 to 80° C. and preferably is at least 50° C. The fully coloured temperature T4 is suitably higher than ambient temperature, preferably higher than 50° C. The fully decolorized temperature T1 is suitably lower than 20° C., preferably lower than 0° C.

The thermochromic composition comprises an electron-donating colouring organic compound (A), an electron-accepting colouring organic compound (B) and (C) a reaction medium.

A wide range of compounds are known for use as a reaction medium (C) in a thermochromic composition and any known or novel reaction medium compounds may be employed.

In a further aspect, the invention provides for the use of a thermochromic composition comprising an electron-donating colouring organic compound (A), an electron-accepting colouring organic compound (B) and (C) a reaction medium (C) in a temperature indicator, preferably a tamper-evident label or a freeze indicator label.

In a preferred embodiment, the reaction medium comprises a compound of formula (I):

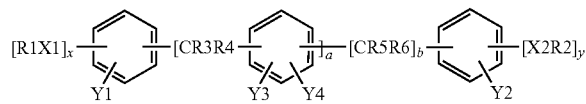

wherein:
- $R_1$, and $R_2$ are independently selected from an optionally substituted linear or branched alkyl group, alkenyl group, alkoxy group, aryl group and an alkylene aryl group; preferably having from 5 to 22 or 6 to 22 carbon atoms, preferably $C_{5-22}$ alkyl or $C_{1-12}$ alkylene or aryl, especially $C_9$ to $C_{17}$ alkyl for example $C_6$alkyl, $C_{10}$ alkyl, $C_{12}$alkyl, $C_{14}$alkyl, $C_{16}$alkyl, $C_{1-4}$ alkylene and phenyl;
- $X_1$ and $X_2$ are independently selected from —OC(O)—, —CO$_2$— and O and preferably $R_1X_1$ and $R_2X_2$ are not —O-alkenyl;
- $R_3$, $R_4$ and $R_5$ are independently selected from hydrogen and an optionally substituted linear or branched hydrocarbyl group, preferably alkyl group, cycloalkyl group, alkenyl group and alkoxy group; especially hydrogen, $C_{1-10}$ alkyl, more preferably hydrogen and $C_{1-4}$ alkyl, for example methyl;
- $R_6$ is selected from hydrogen, halogen $R_3$, —$X_1R_1$, optionally substituted aryl for example phenyl and preferably when $R_6$ is —$X_1R_1$, $R_1$ is not aryl, alkenyl or an alkylene aryl group; $R_6$ is preferably selected from hydrogen, $C_{1-10}$ alkyl and —$CO_2R_1$, more preferably hydrogen and $C_{1-4}$ alkyl, —$CO_2R_1$;
- $Y_1$, Y2, Y3 and Y4 are independently selected from hydrogen, $R_3$, —$OR_3$ and halogen and, in a preferred embodiment —$OR_3$ is not —O-alkenyl; more preferably hydrogen and $C_{1-4}$ alkyl, for example methyl;
- a is 0 to 4; preferably 0 or 1, b is 0 or 1; x and y are independently 0 or 1 provided that where x and y are 0, a is 0 and b is 1 and $R_6$ is —$CO_2R_1$.

Preferably, when a is 0 and b is 1 and $R_5$ or $R_6$ is phenyl, $R_6$ and $R_5$ respectively are not hydrogen or $C_{1-7}$ alkyl.

The term "optionally substituted" as employed herein means that the group or moiety may be substituted with one or more substituents but preferably is unsubstituted. If a substituent is present, it may be selected a group containing a heteroatom but is preferably a hydrocarbyl group containing only hydrogen and carbon atoms. Examples of substituents include nitro, chloro, fluoro, bromo, nitrile, hydroxyl, thiol, a carboxylic acid group, a carboxylic ester group, $C_{1-22}$-alkoxy, $C_{1-22}$-alkyl, $C_{1-22}$-alkenyl, $C_{1-14}$ aryl or $C_{1-6}$ alkaryl, amino, amino $C_{1-22}$-alkyl and amino di ($C_{1-22}$-alkyl).

Examples of alkyl groups include methyl, ethyl, isopropyl, n-propyl, butyl, tert-butyl, n-hexyl, n-decyl, n-dodecyl, cyclohexyl, octyl, iso-octyl, hexadecyl, octadecyl, iso-octadecyl and docosyl. Examples of alkenyl groups include ethenyl, 2-propenyl, cyclohexenyl, octenyl, iso-octenyl, hexadecenyl, octadecenyl, iso-octadecenyl and docosenyl. Examples of alkoxy groups include methoxy, ethoxy, propoxy, tert-butoxy and n-butoxy.

The term aryl refers to a five or six membered cyclic, 8-10 membered bicyclic or 10-14 membered tricyclic group with aromatic character and includes groups which contain only hydrogen and carbon atoms and also heteroaromatic groups which contain hydrogen, carbon and one or more heteroatoms, for example, N, O or S. Examples of suitable aryl groups include phenyl, pyridinyl and furanyl. Where the term "alkylaryl" is employed herein, the immediately preceding carbon atom range refers to the alkyl substituent only and does not include any aryl carbon atoms. Examples of alkaryl groups include benzyl, phenylethyl and pyridylmethyl. Advantageously the aryl group is a phenyl group.

In preferred embodiments, optional substituents are selected from halogen, for example chlorine, halo alkyl, for example $C_{1-6}$ halo alkyl and $C_{1-4}$ alkoxy, for example methoxy The phenyl moieties of compound (I) may independently be unsubstituted where $Y_1$ $Y_2$ $Y_3$ and $Y_4$ are hydrogen or substituted by one or more groups of $Y_1$, $Y_2$, $Y_3$ and $Y_4$ other than hydrogen. Where x or y are 0, the respective phenyl moieties are suitably unsubstituted.

Each aryl ring of compound (I), preferably phenyl ring, may have 2 or more $Y_1$, $Y_2$, $Y_3$ and $Y_4$ substituents respectively. Where one or more aryl ring has 2 or more substituents, the substituents are suitably selected from hydroxyl and $C_{1-4}$ alkyl, preferably methyl.

In one preferred embodiment, the compound (I) has a formula (II) wherein a, b, x and y are 1:

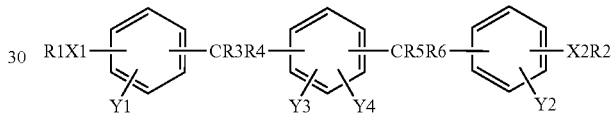

wherein $Y_1$, $Y_2$, $Y_3$, $Y_4$, $R_1$, $R_2$, $R_3$, $R_4$, $R_5$, $R_6$, $X_1$ and $X_2$ are as defined above.

In a preferred embodiment of compound (II), $R_3$, $R_4$, $R_5$ and $R_6$ are independently selected from hydrogen and an optionally substituted linear or branched alkyl group, alkenyl group and alkoxy group having from 5 to 22 carbon atoms and are more preferably independently selected from hydrogen and $C_{1-10}$ alkyl, especially and $C_{1-4}$ alkyl and hydrogen. In an especially preferred embodiment and $R_3$, $R_4$, $R_5$ and $R_6$ are independently selected from hydrogen and methyl and desirably are all methyl. The moieties —$CR_3R_4$— and —$CR_5R_6$— may be in an ortho, meta or para relationship to each other, preferably para or meta. Suitably, the moieties —$CR_3R_4$— and $R_1X_1$— and the moieties —$CR_5R_6$ and $R_2X_2$— respectively may be in an ortho, meta or para relationship to each other, preferably para.

Preferably compound (II) has the following formula compound (III):
Compound (III):

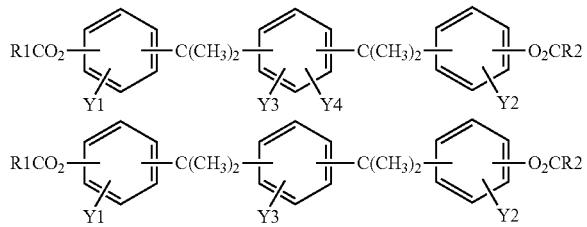

in which $Y_1$, $Y_2$ $Y_3$ and $y_4$ are all hydrogen, and in which $R_1CO_2$— and —$O_2CR_2$ are both in a para position and the two —C(CH$_3$)$_2$— moieties are in a para or meta relationship as shown in formulae (IV) and (V) below. Preferably R$_1$ and R$_2$ are independently selected from C$_9$ to C$_{15}$ alkyl for example C$_{10}$ alkyl.

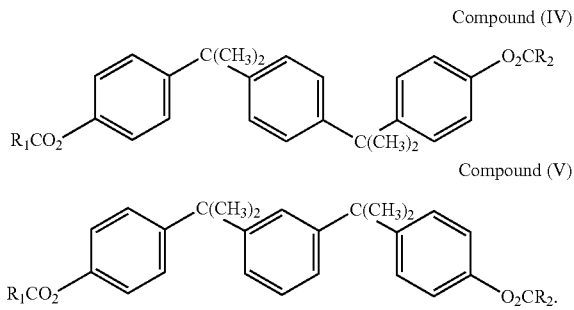

Compound (IV)

Compound (V)

Preferably the compounds of formula (IV) are selected from compounds of formulae (IVa), (IVb) and (IVc) as shown below:

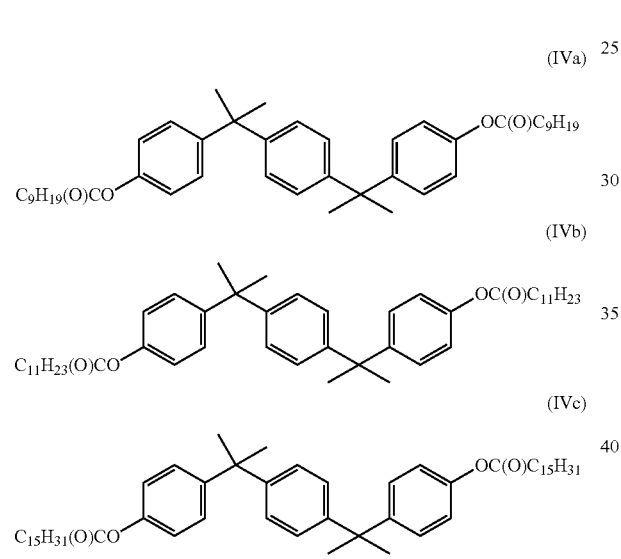

(IVa)

(IVb)

(IVc)

In another preferred embodiment, the compound (I) has a formula (VI) wherein a and b are 0 and x is 1 and y is 0 or 1:

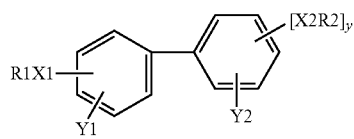

wherein R$_1$, R$_2$, X$_1$, X$_2$, Y$_1$ and Y$_2$ are as defined in relation to the compound of formula I.

Suitably, when y=1, the groups R$_1$X$_1$— and —X$_2$R$_2$ are independently in the ortho or meta position and preferably both are in the ortho position.

We have found that a compound which conformationally is not planar provides an excellent hysteresis width whereas corresponding compounds which are planar do not provide as beneficial hysteresis characteristics. The compound is preferably non planar.

Preferably the compound has a hysteresis width of at least 10 degrees, more preferably at least 20 degrees and desirably at least 30 degrees, for example 40 degrees or more.

Accordingly, the groups R$_1$X$_1$— and —X$_2$R$_2$, where present, are independently in the ortho or meta position to provide a non-planar compound. Corresponding compounds in which the R$_1$X$_1$— and —X$_2$ R$_2$ are in a para position provide much less advantageous hysteresis characteristics. Preferably both groups R$_1$X$_1$— and —X$_2$ R$_2$ are in the ortho position.

In a preferred embodiment, when Y$_1$ and/or Y$_2$ are in the para position Y$_1$ and Y$_2$ are independently selected from hydrogen, halogen and R$_3$, and more preferably hydrogen and C$_{1-4}$ alkyl, for example methyl.

Preferably, R$_1$, R$_2$, Y$_1$ and Y$_2$ do not comprise reactive or conjugated alkylene groups.

In a preferred embodiment, compound (VI) is selected from:

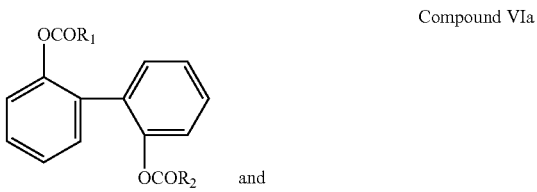

Compound VIa and

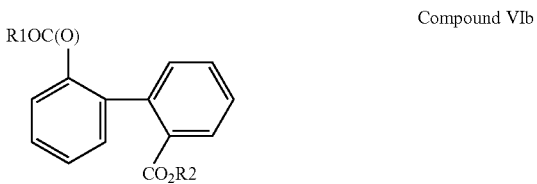

Compound VIb wherein R$_1$ and R$_2$, are independently selected from aryl for example phenyl, C$_{5-22}$ alkyl, preferably C$_{7-22}$ alkyl, especially C$_9$ or C$_{10-18}$ alkyl for example C$_{14}$ alkyl and alkylene aryl of formula —[CH$_2$]$_z$ Ar where z is from 1 to 6 and Ar is optionally substituted phenyl, for example —[CH$_2$]$_2$ C$_6$H$_5$.

In another preferred embodiment the compound of formula (VIa) is a compound of the following formula (VIa1), (VIa2) or (VIa3):

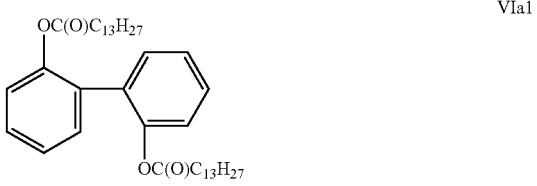

VIa1

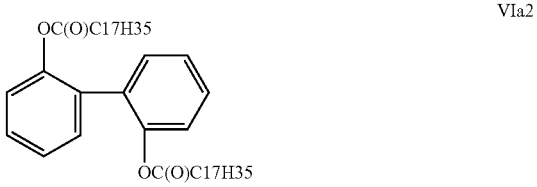

VIa2

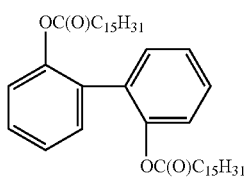

In another preferred embodiment, the compound (1) has a formula (VII) wherein a is 0 and b is 1:

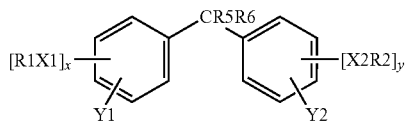

wherein $R_1$, $R_2$, $R_5$, $R_6$, $X_1$, $X_2$, $Y_1$ and $Y_2$ are as defined above. The groups $R_1X_1-$ and $-X_2R_2$, if present, are independently in the ortho, para or meta position and preferably both are in the para position. In a further preferred embodiment, x and y are 0.

In a preferred embodiment of compound (VII) x and y are 0, $R_5$ is H or $C_{1-4}$ alkyl and $R_6$ is $-CO_2R_1$. In another embodiment, R1X1 and R2X2 are in the para position and X1 and X2 are oxygen and Y1 and Y2 are hydrogen, for example as described in WO2010/064447.

The compounds of formula (I) to (VII) as defined above and in particular of formulae (IVa), (IVb), (IVc) and (VIa1) are particularly useful as components of a thermochromic, composition.

Other compounds which are suitable for use as a reaction medium include, but are not limited to compounds of formula:

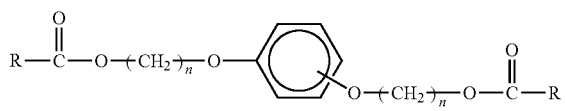

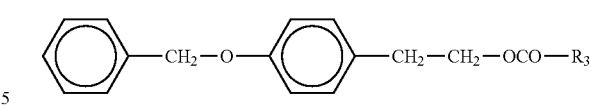

as described in U.S. Pat. No. 7,494,537;

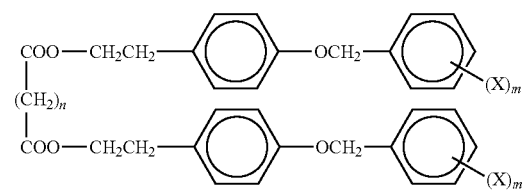

as described in U.S. Pat. No. 8,529,683;

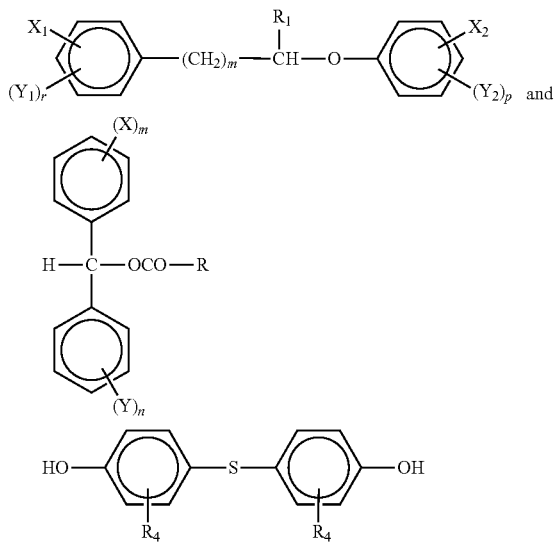

as described in U.S. Pat. No. 7,494,537;

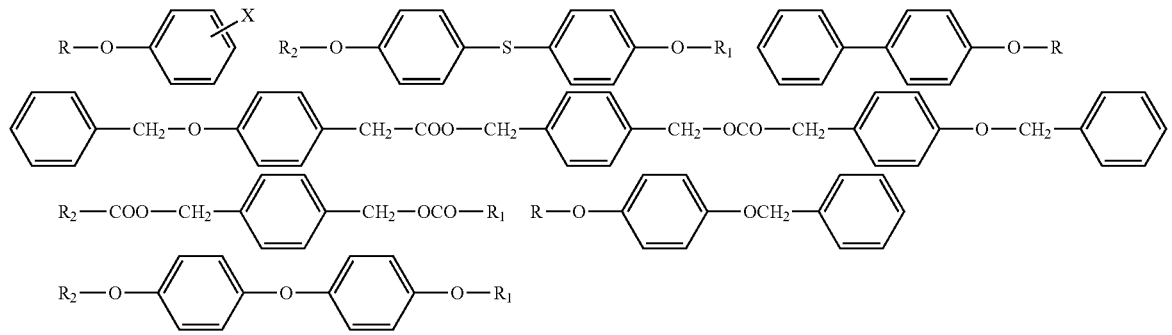

as described in JP2007-118197.

The contents of WO2010/064447, JP2007-118197, U.S. Pat. Nos. 7,494,537, 8,529,683; as and U.S. Pat. No. 8,845,799 are in their entirety incorporated herein by reference.

Any suitable known or future electron donating colouring compounds, component A) of the composition and convenas described in U.S. Pat. No. 8,845,799;

tionally known as a colour former, may be employed. Examples of suitable classes of compounds include indolyles, phthalides, azaphthalides, fluorans, styrylquinoline and diazarhodamine lactones.

Particular examples of component A) include 2'-chloro-6'-diethylaminofluoran, 6'-(diethylamino)-2'-(phenylamino)-3H-spiro[2-benzofuran-1,9'-xanthen]-3-one, 3-(4-diethylamino-2-hexyloxyphenyl)-3-(1-ethyl-2-methylindol-3-yl)-4-azaphthalide, 3,3-bis(p-dimethylaminophenyl)-6-dimethylaminophthalide, 3-(4-diethylaminophenyl)-3-(1-ethyl-2-methylindol-3-yl)phthalide, 3,3-bis(1-n-butyl-2-methylindol-3-yl)phthalide, 3,3-bis(2-ethoxy-4-diethylaminophenyl)-4-azaphthalide, 3-[2-ethoxy-4-(N-ethylanilino)phenyl]-3-(1-ethyl-2-methylindol-3-yl)-4-azaphthalide, 3,6-diphenylaminofluoran, 3,6-dimethoxyfluoran, 3,6-di-n-butoxyfluoran, 2-methyl-6-(N-ethyl-N-p-tolylamino)fluoran, 3-chloro-6-cyclohexylaminofluoran, 2-methyl-6-cyclohexylaminofluoran, 2-(2-chloroanilino)-6-di-n-butylaminofluoran, 2-(3-trifluoromethylanilino)-6-diethylaminofluoran, 2-(N-methylanilino)-6-(N-ethyl-N-p-tolylamino)fluoran, 1,3-dimethyl-6-diethylaminofluoran, 2-chloro-3-methyl-6-diethylaminofluoran, 2-anilino-3-methyl-6-diethylaminofluoran, 2-anilino-3-methyl-6-di-n-butylaminofluoran, 2-xylidino-3-methyl-6-diethylaminofluoran, 1-2-benz-6-diethylaminofluoran, 1,2-benz-6-(N-ethyl-N-isobutylamino)fluoran, 1,2-benz-6-(N-ethyl-N-isoamylamino)fluoran, 2-(3-methoxy-4-dodecoxystyryl)quinoline, spiro[5H-(1)benzopyrano(2,3-d)pyrimidine-5,1'(3'H)isobenzofuran]-3'-one, 2-(diethylamino)-8-(diethylamino)-4-methyl-, spiro[5H-(1)benzopyrano(2,3-d)pyrimidine-5,1'(3'H)isobenzofuran]-3'-one, 2-(di-n-butylamino)-8-(di-n-butylamino)-4-methyl-, spiro[5H-(1)benzopyrano(2,3-d)pyrimidine-5,1'(3'H)isobenzofuran]-3'-one, 2-(di-n-butylamino)-8-(diethylamino)-4-methyl-, spiro[5H-(1)benzopyrano(2,3-d)pyrimidine-5,1'(3'H)isobenzofuran]-3'-one, 2-(di-n-butylamino)-8-(N-ethyl-N-1-amylamino)-4-methyl-, spiro[5H-(1)benzopyrano(2,3-d)pyrimidine-5,1'(3'H)isobenzofuran]-3'-one, 2-(di-n-butylamino)-8-(din-butylamino)-4-phenyl, 3-(2-methoxy-4-dimethylaminophenyl)-3-(1-butyl-2-methylindol-3-yl)-4,5,6,7-tetrachlorophthalide, 3-(2-ethoxy-4-diethylaminophenyl)-3-(1-ethyl-2-methylindol-3-yl)-4,5,6,7-tetrachlorophthalide, and 3-(2-ethoxy-4-diethylaminophenyl)-3-(1-pentyl-2-methylindol-3-yl)-4,5,6,7-tetrachlorophthalide.

Advantageously, component A) is selected from the group consisting of 3-(4-diethylamino-2-hexyloxyphenyl)-3-(1-ethyl-2-methylindol-3-yl)-4-azaphthalide, 2'-chloro-6'-diethylaminofluoran, 6'-(diethylamino)-2'-(phenylamino)-3H-spiro[2-benzofuran-1,9'-xanthen]-3-one, 3,3-bis(1-n-butyl-2-methylindol-3-yl)phthalide and 2-(2-chloroanilino)-6-di-n-butylaminofluoran.

Any suitable known or future electron accepting group component B) of the composition may be employed. Examples of suitable classes of compounds include compounds having labile or active protons, pseudo-acidic compounds, or electron voids. Examples of classes of compounds having active protons include compounds having a phenolic group such as mono- and poly-phenols bearing substituents known in the art and their metal salts.

Examples of suitable component B) compounds include: phenol, o-cresol, tertiary butyl catechol, nonylphenol, n-octylphenol, n-dodecylphenol, n-stearylphenol, p-chlorophenol, p-bromophenol, o-phenylphenol, 4,4'-cyclohexylidenebisphenol, n-butyl p-hydroxybenzoate, n-octyl p-hydroxybenzoate, resorcin, dodecyl gallate, 2,2-bis(4-hydroxyphenyl)propane, 4,4-dihydroxydiphenylsulfone, 1,1-bis(4-hydroxyphenyl) ethane, 2,2-bis(4-hydroxy-3-methylphenyl)propane, bis(4-hydroxyphenyl) sulfide, 1-phenyl-1,1,-bis(4-hydroxyphenyl)ethane, 1,1-bis(4-hydroxyphenyl)-3-methylbutane, 1,1-bis(4-hydroxyphenyl)-2-methylpropane, 1,1-bis(4-hydroxyphenyl)-n-hexane, 1,1-bis(4-hydroxyphenyl)-n-heptane, 1,1-bis(4-hydroxyphenyl)-n-octane, 1,1-bis(4-hydroxyphenyl)-n-nonane, 1,1-bis(4-hydroxyphenyl)-n-decane, 1,1-bis(4-hydroxyphenyl)-n-dodecane, 2,2-bis(4-hydroxyphenyl)butane, 2,2-bis(4-hydroxyphenyl)ethyl propionate, 2,2-bis(4-hydroxyphenyl)-4-methylpentane, 2,2-bis(4-hydroxyphenyl)hexafluoropropane, 2,2-bis(4-hydroxyphenyl)-n-heptane, 2,2-bis(4-hydroxyphenyl)-n-nonane, 4,4',4"-methylidenetrisphenol, 2,6-bis[(2-hydroxy-5-methylphenol)methyl]-4-methylphenol, 4,4'-[1-[4-[1-(4-hydroxyphenyl)-1-methylethyl]phenyl]ethylidene]bisphenol, 4,4',4"-methylidenetris[2-methylphenol], 4,4'-[(2-hydroxyphenyl)methylene]bis[2,3,6-triphenylphenol], 2,2-methylenebis[6-[(2-hydroxy-5-methylphenyl)methyl]-4-methylphenol], 2,4,6-tris(4-hydroxyphenyl-methyl)1,3-benzenediol, 4,4',4"-ethylidenetrisphenol, 4,4'-[(4-hydroxyphenyl)methylene]bis[2-methylphenol], 4,4-[(4-hydroxyphenyl)methylene]bis[2,6-dimethylphenol], 4,4'-[(4-hydroxyphenyl)methylene]bis[2-methylphenol], 4,4'-[(4-hydroxyphenyl)methylene]bis[2,6-dimethylphenol], 4,4'-[(4-hydroxy-3-methoxyphenyl)methylene]bis[2,6-dimethylphenol], 2,4-bis[(5-methyl-2-hydroxyphenyl)methyl]-6-cyclohexylphenol, 4,4'-[1-[4-[1-(4-hydroxy-3-methylphenol)-1-methylethyl]phenyl]ethylidene]bis[2-methylphenol], 4,4'-[(4-hydroxyphenyl)methylene]bis[2-cyclohexyl-5-methylphenol], 4,6-bis[(4-hydroxyphenyl)methyl]1,3-benzenediol, 4,4'-[(3,4-dihydroxyphenyl)methylene]bis[2,6-dimethylphenol], 4,4'-(1-phenylethylidene)bisphenol, 5,5'-(1-methylethylidene)bis[1-phenyl-2-ol], 4,4',4"-methylidenetrisphenol, 4,4'-[1-[4-[1-(4-hydroxyphenyl)-1-methylethyl]phenyl]ethylidene]bisphenol, 4,4'-(phenylmethylene)bisphenol, 4,4'-[1,4-phenylenebis(1-methylethylidene)]bis[2-methylphenol], 5,5'-(1,1-cyclohexylidene)bis[1-biphenyl-2-ol], bis(3-methyl-4-hydroxyphenyl)sulfide, bis(3,5-dimethyl-4-hydroxyphenyl), bis(3-ethyl-4-hydroxyphenyl)sulfide, bis(3,5-diethyl-4-hydroxyphenyl)sulfide, bis(3-propyl-4-hydroxyphenyl)sulfide, bis(3,5-dipropyl-4-hydroxyphenyl)sulfide, bis(3-t-butyl-4-hydroxyphenyl)sulfide, bis(3,5-t-butyl-4-hydroxyphenyl)sulfide, bis(3-pentyl-4-hydroxyphenyl)sulfide, bis(3-hexyl-4-hydroxyphenyl)sulfide, bis(3-heptyl-4-hydroxyphenyl)sulfide and bis(5-octyl-2-hydroxyphenyl)sulfide.

Advantageously component B) can be a mixture of at least two of the above-mentioned component. Advantageously component B) is selected from the group consisting of 2,2-bis(4'-hydroxyphenyl)hexafluoropropane, 1,1-bis(4'-hydroxyphenyl)-2-methylpropane and mixture thereof, more advantageously it is a mixture of 2,2-bis(4'-hydroxyphenyl)hexafluoropropane and 1,1-bis(4'-hydroxyphenyl)-2-methylpropane Suitably, the ratio of components B) to C) In parts by weights is in the range 0.5 to 40 and preferably within 1 to 20. The ratio of components A) to C) In parts by weights is suitably in the range 0.5 to 30 and preferably within 1 to 20.

Each component may comprise 2 or more components. Conventional additives for example emulsifiers, antioxidants, UV absorbers, metal chelates may also be included in the composition.

Suitably the thermochromic composition includes a non-ionic surfactant in the composition, improved stability against colour change when the composition is subjected to pressure in the clear state may be secured.

The term "surfactant" refers to a compound which has a hydrophilic group or region and a hydrophobic group or region. The non-ionic surfactant is preferably an alkoxylate which has a hydrophobic terminal group.

The hydrophobic terminal group is suitably a hydrocarbyl and preferably an alkyl, group. The alkyl group is preferably a $C_1$ to $C_{22}$ group, more preferably $C_7$ to $C_{22}$ especially a $C_9$ to $C_{15}$ group for example a mixed $C_9/C_{11}$ group and a mixed $C_{13}/C_{15}$ group. The alkyl group is suitably derived from an alcohol or an amine, preferably a primary amine.

The alkoxylate is suitably based on multiple units of alkylene oxide and is preferably an ethoxylate, a propoxylate, a butoxylate or a mixture of two or more alkoxylates. Preferably the alkoxylate is an ethoxylate. The mixture may be a random or block arrangement of the different alkoxylates. The alkoxylate preferably comprises from 2 to 30, more preferably 2 to 15 and desirably 3 to 12 alkylene oxide units.

Suitably the non-ionic surfactant has a formula Q:

R'[Het][(CH$_2$)$_q$O]$_r$R"    (Q)

wherein R' is a hydrocarboyl, for example an alkyl group, alkenyl group, aryl group and alkylaryl group having from 1 to 22 carbon atoms, more preferably a $C_1$ to $C_{22}$ group, more preferably a $C_7$ to $C_{22}$ and especially a $C_9$ to $C_{15}$ alkyl, alkenyl or alkylaryl group; Het is O, S or NH or NR'; g is 2 to 4, preferably 2; r is 2 to 30, preferably 3 to 12; and R" is selected independently from R' and H.

The non-ionic surfactant may be "end-capped" which refers to the case where R" is selected from the substituents defining R'. The terminal groups R' and R" may be the same or different.

Suitably, the non-ionic surfactant has a molecular weight from 300 to 1500, preferably 500 to 1000. Preferably the non-ionic surfactant comprises an alcohol alkoxylate. Examples of suitable non-ionic surfactants include those available under the BIOSOFT trade name from Stepan, the LUTENSOL trade name from BASF, the EMULSOGEN and GENAPOL trade names from Clariant and products available under the EMPILAN, HYDRAPOL, SURFONIC, BIONIC and TERIC trade names from Huntsman The thermochromic composition employed in the product of the invention suitably comprises a homogeneous solubilised mixture of the components A), B) and C) of the composition. Preferably, components A) and B) are dissolved in component C) to produce the composition.

US 2010/075253 describes phenol-based compounds that may be employed in the synthesis of Bisphenol P and Bisphenol M and analogues thereof.

Bisphenol P may be produced by reacting:

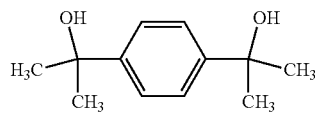

or an analogue thereof with phenol for example as set out in Stetson, Christopher M.; Nishikawa, Shiro; Purkiss, David W.; Dalley; Bartsch, Richard A. Journal of Physical Organic Chemistry, 2005, vol. 18, #11 p. 1107-1115 or as described in Hung; Werbel European Journal of Medicinal Chemistry, 1983, vol. 18, #1 p. 61-66. For analogues, with other substituents, a corresponding aromatic compound may be employed.

The synthesis of Bisphenol M is described in U.S. Pat. No. 6,326,522 B1. WO2015/033750 describes compounds of formula:

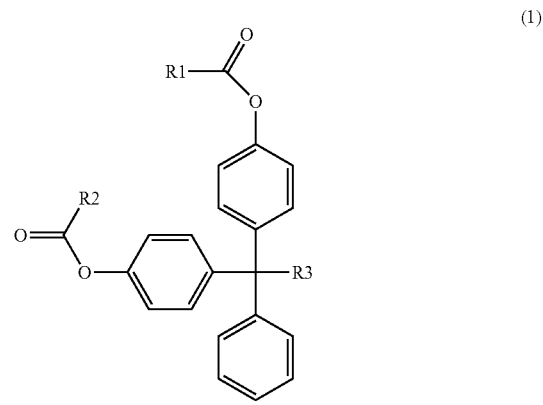

(1)

in which R1 and R2 independently have 7 to 21 carbon atoms and R3 is hydrogen or an alkyl group having 1 to 7 carbon atoms.

U.S. Pat. Nos. 3,979,462 and 6,992,166 describe the synthesis of compounds of the general formula below:

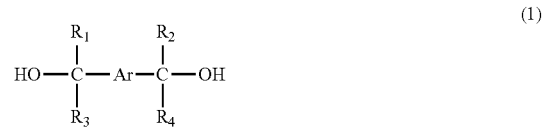

(1)

in which Ar represents an aromatic group having 6 to 20 carbon atoms, $R_1$ to $R_4$ independently represent hydrogen, an alkyl group having 1 to 20 carbon atoms, a cycloalkyl group having 5 to 20 carbon atoms or an aralkyl group having 7 to 20 carbon atoms in which $R_1$ and $R_3$ do not simultaneously represent hydrogen and $R_2$ and $R_4$ do not simultaneously represent hydrogen.

Where Component C is a biphenyl product of formula (VI), is suitably synthesised by stirring a mixture of 1 mole of biphenol and 2.5 moles of triethyl amine in acetone and cooling to 5° C. 2.2 moles of acid chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. Suitably, the relative quantities of biphenol/acid chloride/triethylamine are 1/2.2/2.5 moles. Biphenol is available from Chemos (Germany).

U.S. 64/412,4881 and Wiley Organics "Preparation of biphenols by oxidative coupling of alkylphenols using copper catalyst" describe the synthesis of biphenols.

Suitably, the colour-change composition is microencapsulated to provide a colour-change microcapsule pigment by a known method.

The temoperature-indicator product suitably comprises a colour-change microencapsulated pigment comprising a composition as defined herein which is microencapsulated. Suitably, the composition is homogeneous. Preferably the composition comprises components A), B), C) and a non-ionic surfactant to provide improved stability or resistance to colour-change in the clear state as described above.

The microcapsules suitably have a particle size from 0.5 to 50 microns, preferably 1 to 20 microns so as to provide suitable dispersion stability and processing characteristics whilst providing high density colour.

Unless otherwise stated, all particle sizes referred to herein are measured by volume using a Coulter particle size analyser by laser diffraction, All figures given for particle size represents the 90% fraction of particles showing diameter no larger than the specified size.

The composition may be microencapsulated by any known method, for example by using isocyanate interfacial polymerisation, melamine or urea formaldehyde interfacial polymerisation, free radical interfacial polymerisation, polycondensation of epoxy or complex coacervation.

Microencapsulation allows the colour-change composition to retain its composition when in contact with chemicals or heat. Chemicals are blocked by the microcapsule walls and the formulation of the composition is retained. The microencapsulation may also have a practical benefit on the way the colour-change composition performs.

Figure 1:
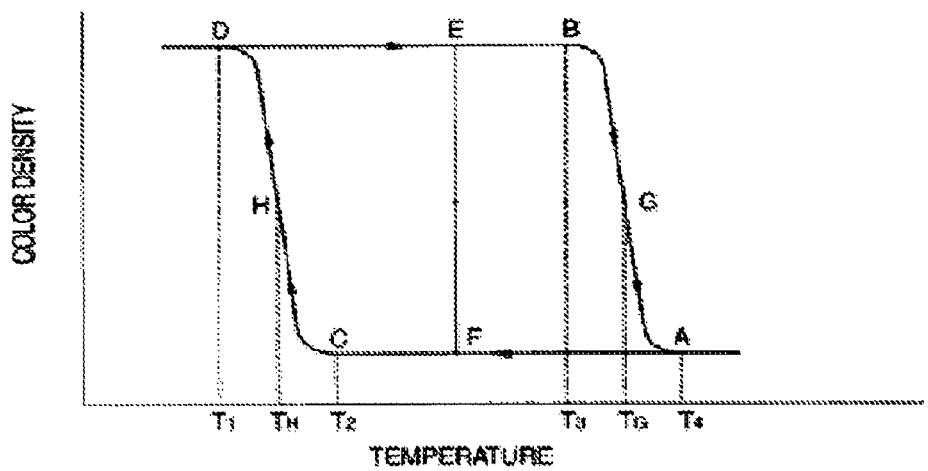
FIG. 1 shows a typical plot of changes in colour density against temperature for thermochromic compositions.

FIG. 1 of the accompanying drawings shows a typical hysteresis profile for a reversible colour-change composition. Colour density is plotted against temperature. The colour density advancement due to temperature change on heating and cooling cycles is illustrated and progresses in the direction of the arrow. Point A at T4 is the fully decolourised state (herein will be called fully decolorized temperature); point B at T3 is the point at which the composition is in a fully coloured state during heating. Point C shows the last point at which the composition is fully discoloured during cooling at T2; Point D is the point at which the composition is in a fully coloured state during cooling at T1 ((herein will be called fully coloured temperature). It will be apparent that the thermochromic composition may be in fully coloured state or a fully discoloured state at a said temperature between T2 and T3 depending on whether the composition is being heated from a lower temperature or cooled form a higher temperature. The difference between temperatures T3 and T2 ($\Delta H_{T3-T2}$) is the practical value for hysteresis (herein will be called practical hysteresis).

The difference between T1 and T2 ($\Delta H_{T2-T1}$) is related to the sensitivity of the colour change mechanism. The lower the value of $\Delta H_{T2-T1}$, the sharper the transition between the last point of the fully coloured state and the fully discoloured state and also the sharper the transition between last point of the fully discoloured state and the fully coloured state.

Colour density difference or colour contrast is measured by the difference of colour between E and F as shown in FIG. 1.

Figure 2A:
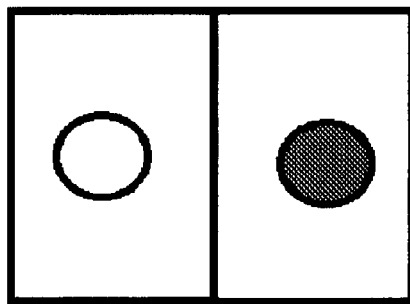
FIGS. 2a to 2c show a temperature freezing indicator label according to the invention based on a memory composition according to the invention.
Figure 2B:
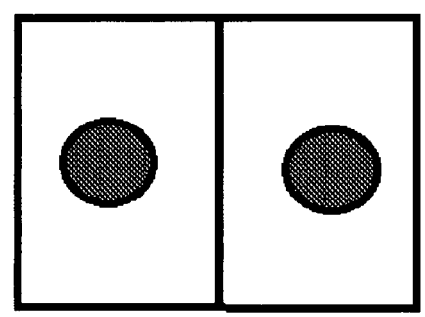
Figure 2C:
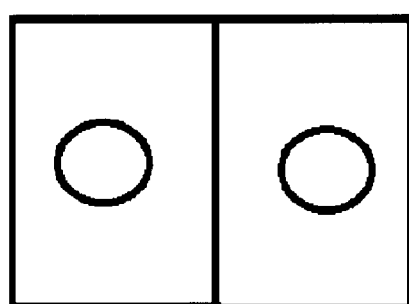

By way of illustration, in the initial state at ambient temperature above T2 and below T3 is represented in FIG. 2a. As the temperature drops below the temperature T2, and is kept below T4 at all times, the state of the indicator changes to that shown in FIG. 2b. By raising the temperature to greater than T3 the indicator provides two colourless compositions as shown in FIG. 2c.

Figure 3A:
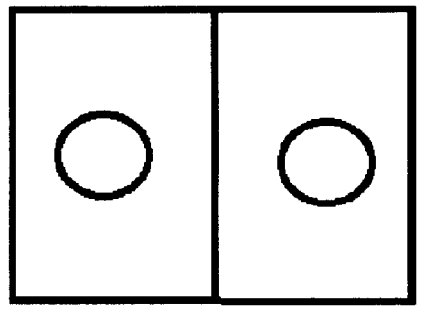
FIGS. 3a to 3c show examples of a temperature indicator label according to the invention based on a memory composition containing Kromagen ink according to the invention.
Figure 3B:
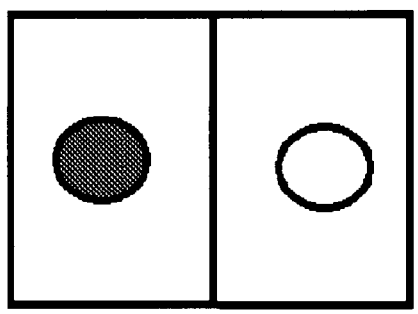
Figure 3C:
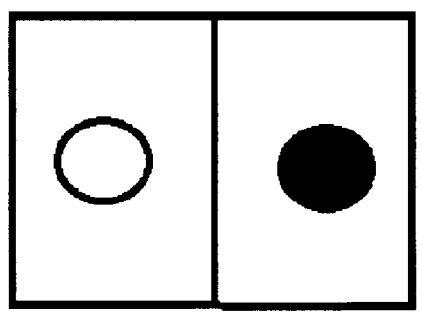

By way of illustration, FIGS. 3a, 3b and 3c illustrate the various forms of the temperature indicator product where the indicator comprises a thermochromic composition as described herein and further comprises Kromagen ink. FIG. 3a shows the initial state at ambient temperature above T2 and below the temperature of colour transition of Kromagen. FIG. 3b shows the indicator as the temperature drops below T2 and below the temperature at which Kromagen changes colour and FIG. 3c shows the indicator as it appears after heating above T4.

The invention is now illustrated by the following non-limiting examples in which parts are by weight unless otherwise stated.

Example 1

A thermochromic colour memory composition was obtained by homogeneously compatibilizing:

4 parts of 3-(4-diethylamino-2-hexyloxyphenyl)-3-(1-ethyl-2-methylindol-3-yl)-4-azaphthalide (component A)) available from Yamada Chemicals and 6 parts 2,2-bis(4'-hydroxyphenyl)hexafluoropropane and 6 parts of 1,1-bis(4'-hydroxyphenyl)-2-methylpropane (both components B)) available from Sigma Aldrich and 84 parts of 4,4'-[1,4-Phenylenebis(1-methylethylydene)]bis(4-phenyldecanoate) (Component C, specifically component IVa) as shown below):

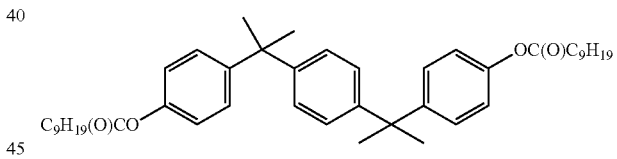

Component IVa is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of decanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above T4. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

Example 2

A thermochromic colour memory composition was obtained by homogeneously compatibilizing:

4 parts of 3,3-bis(1-n-butyl-2-methylindol-3-yl)phthalide (Component A)) available from Yamamoto Chemicals and 6 parts 2,2-bis(4'-hydroxyphenyl)hexafluoropropane and 6 parts of 1,1-bis(4'-hydroxyphenyl)-2-methylpropane (both Component B)) available from Sigma Aldrich and 84 parts of 4,4'-[1,4-Phenylenebis(1-methylethylydene)]bis(4-phenyldodecanoate) (Component C) specifically component IVb) as shown below):

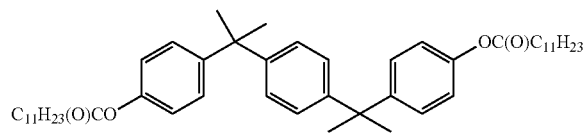

Component IVb was prepared using the same procedure as described in Example 1 for Component IVa save that dodecanoyl chloride was employed rather than decanoyl chloride.

The resulting memory composition changed colour from magenta to colourless. The thermochromic colour memory composition was heated above T4. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours.

The resulting dispersion was then drum dried and the pigment was isolated in encapsulated form, the thermochromic colour memory pigment having a particle size of 2.5 microns changed colour from magenta to colourless.

Example 3

A thermochromic colour memory composition was obtained by homogeneously compatibilizing:

4 parts of 2-(2-chloroanilino)-6-di-n-butylaminofluoran (Component A)) available from Hodogaya Chemical Co. Ltd. and 6 parts 2,2-bis(4'-hydroxyphenyl)hexafluoropropane and 6 parts of 1,1-bis(4'-hydroxyphenyl)-2-methylpropane (Component B)) available from Sigma Aldrich and 84 parts of 4,4'-[1,4-Phenylenebis(1-methylethylydene)]bis(4-phenylhexadecanoate) (Component C) specifically component IVc) as shown below). The resulting memory composition changed colour from black to colourless.

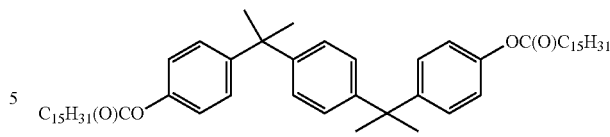

Component IVc was prepared using the same procedure as described in Example 1 for Component IVa save that hexadecanoyl chloride was employed rather than decanoyl chloride.

The thermochromic colour memory composition was heated above T4. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours.

The resulting dispersion was then air dried and the pigment was isolated in encapsulated form, the thermochromic colour memory pigment having a particle size of 4 microns changed colour from black to colourless.

Example 4

A thermochromic colour memory composition was obtained by homogeneously compatibilizing:

4.1 parts of 3-Diethylamino-6-methyl-7-(2,4-xylidino)fluoran (component A) available from Yamamoto Chemicals and 4.75 parts 4,4'-Cyclohexylidenebisphenol and 4.75 parts of 4-Hydroxyphenyl-4'-isopropoxyphenyl sulfone (both components B) available from Sigma Aldrich and 86.4 parts of 4,4'-[1,4-Phenylenebis(1-methylethylydene)]bis(4-phenyldecanoate) (Component C, specifically component IVa) as shown below):

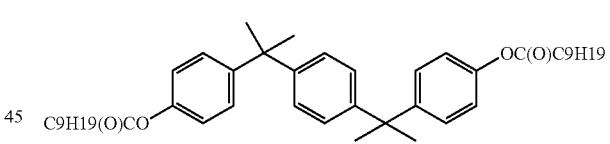

Component IVa is synthesised as per example 1

The resulting memory composition changed colour from black to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Example 5

A thermochromic colour memory composition was obtained by homogeneously compatibilizing:

4.1 parts of 3,3-Bis(1-butyl-2-methylindol-3-yl)phthalide (component A) available from Yamamoto Chemicals and 5.3 parts 4,4'-Cyclohexylidenebisphenol and 4.1 parts of 4,4'-(1-Phenylethylidene)bisphenol (both components B)) available from Sigma Aldrich and 86.5 parts of 4,4'-[1,4-Phenylenebis(1-methylethylydene)]bis(4-phenyldecanoate) (Component C, specifically component IVa) as shown below)

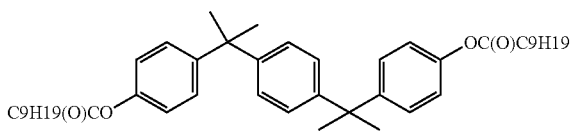

Component IVa is synthesised as per example 1

The resulting memory composition changed colour from magenta to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Example 6

A thermochromic colour memory composition was obtained by homogeneously compatibilizing:

4.1 parts of 3,3-bis(2-ethoxy-4-diethylaminophenyl)-4-azaphthalide (component A) available from Yamamoto Chemicals and 3 parts 4,4'-Cyclohexylidenebisphenol, 6.5 parts of 4,4'-(1-Phenylethylidene)bisphenol, 2 parts of 4,4'-Thiodiphenol and 2 parts of 2-hydroxy-4-methoxy benzophenone (all components B)) available from Sigma Aldrich and 82.4 parts of 4,4'-[1,4-Phenylenebis(1-methylethylydene)]bis(4-phenyldecanoate) (Component C, specifically component IVa) as shown below)

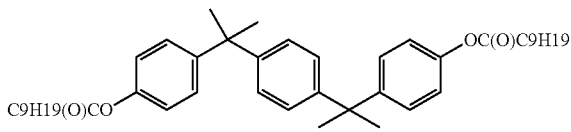

Component IVa is synthesised as per example 1

The resulting memory composition changed colour from turquoise to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Example 7

A thermochromic colour memory composition was obtained by homogeneously compatibilizing:

7 parts 2'-chloro-6'-diethylaminofluoran (component A) available from Yamamoto Chemicals and 6 parts 4,4'-Cyclohexylidenebisphenol, 6 parts of 4,4'-(1-Phenylethylidene)bisphenol, 4 parts of 4,4'-Thiodiphenol and 2 parts of 2-hydroxy-4-methoxy benzophenone (all components B)) available from Sigma Aldrich and 75 parts of 4,4'-[1,4-Phenylenebis(1-methylethylydene)]bis(4-phenyldecanoate) (Component C, specifically component IVa) as shown below):

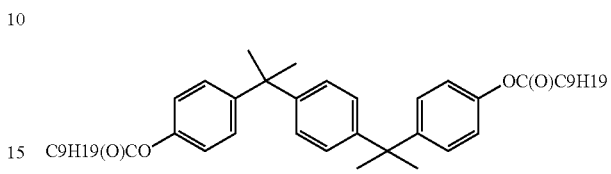

Component IVa is synthesised as per example 1

The resulting memory composition changed colour from red to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Example 8

A thermochromic colour memory composition was obtained by homogeneously compatibilizing:

3.1 parts of 6'-(diethylamino)-2'-(phenylamino)-3H-spiro[2-benzofuran-1,9'-xanthen]-3-one (component A) and 5.1 parts 4,4'-Cyclohexylidenebisphenol, 5.1 parts of 4,4'-(1-Phenylethylidene)bisphenol and 1.9 parts of 2-hydroxy-4-methoxy benzophenone (all components B) available from Sigma Aldrich and 84.8 parts of 4,4'-[1,4-Phenylenebis(1-methylethylydene)]bis(4-phenyldecanoate) (Component C, specifically component IVa) as shown below)

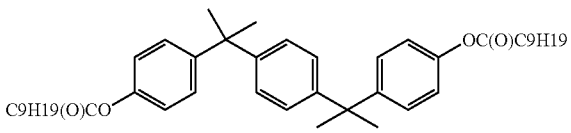

Component IVa is synthesised as per example 1

The resulting memory composition changed colour from green to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Example 9

A thermochromic colour memory composition was obtained by homogeneously compatibilizing:

3 parts of 3-(4-diethylamino-2-hexyloxyphenyl)-3-(1-ethyl-2-methylindol-3-yl)-4-azaphthalide (component A) available from Yamada Chemicals and 12.6 parts 4,4'-Isopropylidenedi-o-cresol available from Sigma Aldrich (components B) and 84.4 parts of 4,4'-[1,4-Phenylenebis(1-methylethylydene)]bis(4-phenylundecanoate) (Component C, specifically component IVd) as shown below):

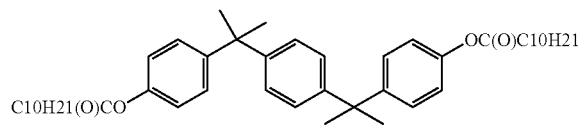

Component IVd is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of undecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether—maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

Example 10

A thermochromic colour memory composition was obtained by homogeneously compatibilizing:

4 parts of 3-(4-diethylamino-2-hexyloxyphenyl)-3-(1-ethyl-2-methylindol-3-yl)-4-azaphthalide (component A)) available from Yamada Chemicals, 6.4 parts 2,2-bis(4'-hydroxyphenyl)hexafluoropropane and 6.4 parts of butyl 4-hydroxybenzoate available from Sigma Aldrich (both components B) and 83.2 parts of 4,4'-[1,4-Phenylenebis(1-methylethylydene)]bis(4-phenyltetradecanoate) (Component C, specifically component IVe) as shown below):

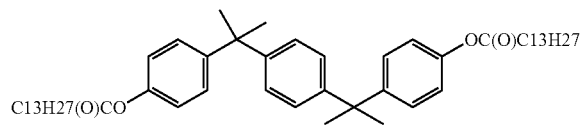

Component IVe is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of tetradecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

Example 11

A thermochromic colour memory composition was obtained by homogeneously compatibilizing:

4.1 parts of 3-(4-diethylamino-2-hexyloxyphenyl)-3-(1-ethyl-2-methylindol-3-yl)-4-azaphthalide (component A) available from Yamada Chemicals, 4.85 parts 2,2-bis(4'-hydroxyphenyl)hexafluoropropane, 4.85 parts 4,4'-(1-Phenylethylidene)bisphenol and 8.6 parts of lauric acid (all components B) available from Sigma Aldrich and 77.6 parts of 4,4'-[1,4-Phenylenebis(1-methylethylydene)]bis(4-phenylhexanoate) (Component C, specifically component IVf) as shown below)

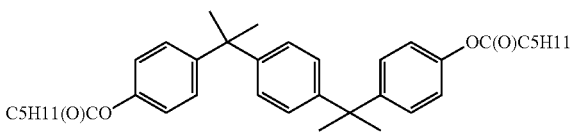

Component IVf is suitably synthesised by stirring a mixture of 1 mole of 4,4'-(1,4-Phenylenediisopropylidene) bisphenol, commercially available from Mitsui Chemicals, and 2.5 moles of triethyl amine in acetone and cooling to 5° C. 2.2 moles of hexanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether—maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

Example 12

A thermochromic colour memory composition was obtained by homogeneously compatibilizing:

4.15 parts of 3-(4-diethylamino-2-hexyloxyphenyl)-3-(1-ethyl-2-methylindol-3-yl)-4-azaphthalide (component A)) available from Yamada Chemicals and 4.85 parts 2,2-bis(4'-hydroxyphenyl)hexafluoropropane and 4.85 parts of 1,1-bis(4'-hydroxyphenyl)-2-methylpropane (both components B)) available from Sigma Aldrich and and 86.15 parts of 4,4'-[1,3-Phenylenebis(1-methylethylydene)]bis(4-phenylhexadecanoate) (Component C, specifically component Va) as shown below):

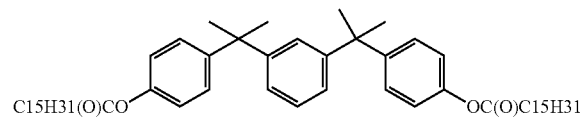

Component Va is suitably synthesised by stirring a mixture of 1 mole of 4,4'-(1,3-Phenylenediisopropylidene)bisphenol, commercially available from Mitsui Chemicals, and 2.5 moles of triethyl amine in acetone and cooling to 5° C. 2.2 moles of hexadecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

Example 13

A thermochromic colour memory composition was obtained by homogeneously compatibilizing:

4.1 parts of 3-(4-diethylamino-2-hexyloxyphenyl)-3-(1-ethyl-2-methylindol-3-yl)-4-azaphthalide (component A) available from Yamada Chemicals, 4.85 parts 4,4'-(1-Phenylethylidene)bisphenol and 4.85 parts 4,4'-Isopropylidenedi-o-cresol available from Sigma Aldrich (both components B) and 86.2 parts of 4,4'-[1,3-Phenylenebis(1-methylethylydene)]bis(4-phenyltetradecanoateanoate) (Component C, specifically component Vb) as shown below)

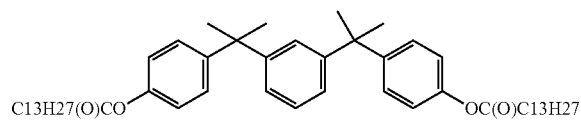

Component Va is suitably synthesised by stirring a mixture of 1 mole of 4,4'-(1,3-Phenylenediisopropylidene)bisphenol, commercially available from Mitsui Chemicals, and 2.5 moles of triethyl amine in acetone and cooling to 5° C. 2.2 moles of tetradecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of bisphenol/acid chloride/triethylamine are 1/2.2/2.5 moles.

The resulting memory composition changed colour from blue to colourless.

The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Some of the resulting dispersion was then drum dried and the pigment in encapsulated form was isolated, the thermochromic colour memory pigment having a particle size of 2 microns changed colour from blue to colourless.

Example 14

A thermochromic colour memory composition was obtained by homogeneously compatibilizing:

3.1 parts of 6'-(diethylamino)-2'-(phenylamino)-3H-spiro[2-benzofuran-1,9'-xanthen]-3-one (component A) and 5.1 parts 4,4'-Cyclohexylidenebisphenol, 5.1 parts of 4,4'-(1-Phenylethylidene)bisphenol and 1.9 parts of 2-hydroxy-4-methoxy benzophenone (all components B) available from Sigma Aldrich and 70 parts of 4,4'-[1,4-Phenylenebis(1-methylethylydene)]bis(4-phenyldecanoate) and 14.8 parts of 4,4'-[1,4-Phenylenebis(1-methylethylydene)]bis(4-phenyloctanoate) (Components C, respectively component IVa and IVg as shown below):

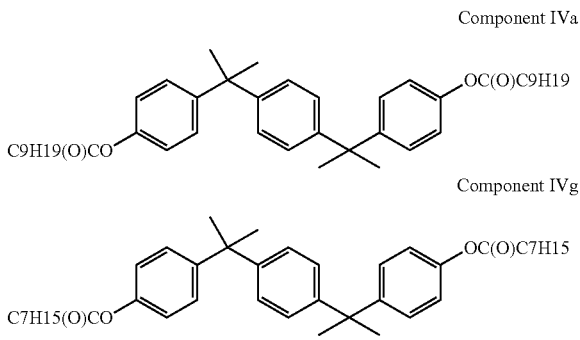

Component IVa

Component IVg

The resulting memory composition changed colour from green to colourless.

The thermochromic colour memory composition was heated above 100 degrees. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours.

Example 15

A thermochromic colour memory composition was obtained by homogeneously compatibilizing:

4 parts of 3-(4-diethylamino-2-hexyloxyphenyl)-3-(1-ethyl-2-methylindol-3-yl)-4-azaphthalide (electron donating compound) available from Yamada Chemicals and 6 parts 2,2-bis(4'-hydroxyphenyl)hexafluoropropane and 6 parts of 1,1-bis(4'-hydroxyphenyl)-2-methylpropane (both electron accepting compounds) available from Sigma Aldrich and 84 parts of compound (VI a1) 2,2' biphenyl bistetradecanoate ester as shown below:

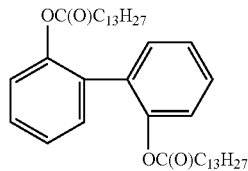

Component VIa1 is suitably synthesised by stirring a mixture of 1 mole of 2,2'-Dihydroxybiphenyl, which is available from Sigma Aldrich or may be prepared using the method described by B. Schmidt, M. Riemer, and M. Karras (J. Org. Chem., 2013, 78 (17), pp 8680-8688), and 2.5 moles of triethyl amine in acetone and cooling to 5° C. 2.2 moles of acid chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of biphenol/acid chloride/triethylamine are 1/2.2/2.5 moles.

The resulting memory composition changed colour form blue to colourless. The thermochromic colour memory composition was heated above T4. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above T4 and slowly added 25 parts of a solution of melamine formaldehyde resin. The resulting emulsion was stirred and heated to a temperature of 80° C. for 6 hours. Some of the resulting dispersion was then drum dried and the pigment was isolated in encapsulated form, the thermochromic colour memory pigment having a particle size of 1.5 microns changed colour from blue to colourless.

Example 16

4.1 parts of 3-(4-diethylamino-2-hexyloxyphenyl)-3-(1-ethyl-2-methylindol-3-yl)-4-azaphthalide (electron donating compound) available from Yamada Chemicals and 4.85 parts 2,2-bis(4'-hydroxyphenyl)hexafluoropropane and 4.85 parts of 1,1-bis(4'-hydroxyphenyl)-2-methylpropane (both electron accepting compounds) available from Sigma Aldrich and 86.2 parts of compound (VI a2) 2,2' biphenyl bisoctadecanoate ester as shown below:

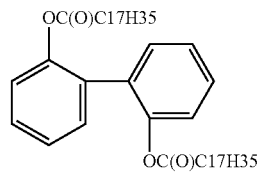

Component VIa2 is suitably synthesised by stirring a mixture of 1 mole of 2,2'-Dihydroxybiphenyl, which is available from Sigma Aldrich or may be prepared using the method described by B. Schmidt, M. Riemer, and M. Karras (J. Org. Chem., 2013, 78 (17), pp 8680-8688), and 2.5 moles of triethyl amine in acetone and cooling to 5° C. 2.2 moles of octadecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of biphenol/acid chloride/triethylamine are 1/2.2/2.5 moles.

The resulting memory composition changed colour form blue to colourless. The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours. Some of the resulting dispersion was then drum dried and the pigment was isolated in encapsulated form, the thermochromic colour memory pigment having a particle size of 2.1 microns changed colour from blue to colourless.

Example 17

4.1 parts of 3-(4-diethylamino-2-hexyloxyphenyl)-3-(1-ethyl-2-methylindol-3-yl)-4-azaphthalide (electron donating compound) available from Yamada Chemicals and 4.85 parts 2,2-bis(4'-hydroxyphenyl)hexafluoropropane and 4.85 parts of 1,1-bis(4'-hydroxyphenyl)-2-methylpropane (both electron accepting compounds) available from Sigma Aldrich and 86.2 parts of compound (VI a3) 2,2' biphenyl bishexadecanoate ester as shown below:

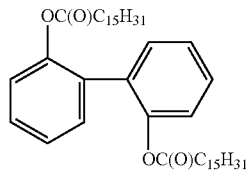

Component VIa3 is suitably synthesised by stirring a mixture of 1 mole of 2,2'-Dihydroxybiphenyl, which is available from Sigma Aldrich or may be prepared using the method described by B. Schmidt, M. Riemer, and M. Karras (J. Org. Chem., 2013, 78 (17), pp 8680-8688), and 2.5 moles of triethyl amine in acetone and cooling to 5° C. 2.2 moles of hexadecanoyl chloride is added gradually so that temperature does not rise above 35° C. during the addition. After the addition is complete the reaction is brought to room temperature and stirred for 24-48 hours. The resulting reaction medium is then poured into 7% aqueous ice cold HCl. The precipitate is filtered off and washed with water and saturated sodium bicarbonate solution. The solid precipitate is crystallised from isopropanol. The relative quantities of biphenol/acid chloride/triethylamine are 1/2.2/2.5 moles.

The resulting memory composition changed colour form blue to colourless. The thermochromic colour memory composition was heated above 100° C. 100 parts of the hot thermochromic colour memory composition was then dispersed into 100 parts of a 10% solution of methyl vinyl ether-maleic anhydride copolymerized resin neutralised with sodium hydroxide to pH 4 by means of a high speed homogeniser. The resulting emulsion was maintained at temperature above 80° C. and slowly added 25 parts of a solution of melamine formaldehyde resin. The resulting emulsion was stirred and heated to a temperature of 80° C. for 6 hours. Some of the resulting dispersion was then drum dried and the pigment was isolated in encapsulated form, the thermochromic colour memory pigment having a particle size of 2.5 microns changed colour from blue to colourless.

Preparation of the Measuring Samples 10 parts of the thermochromic colour memory composition of the water dispersion obtained in Example 1 in encapsulated form were dispersed in 10 parts of a polyvinyl alcohol solution was screen printed onto sheet of copy paper, thereby obtaining a test sample.

The same method has been carried out in order to obtain a test sample for the thermochromic colour memory composition of Examples 2 to 17 in encapsulated form. Each of the test samples was heated and cooled by the below described method. The measuring sample thus prepared was set on a predetermined position of a Linkam (manufactured by linkam, UK) and the colour density at each temperature was measured by heating and cooling at a rate of 5° C./min with a temperature width of 100° C.

For example, in the case of Example 1, the sample was heated up to 100° C. at a rate of 5° C./min from a measurement starting temperature of 0° C., and then cooled to −20° C. at a rate of 5° C./min. The brightness of the colour displayed at each temperature was plotted on a graph to prepare the colour density-temperature curve as illustrated in FIG. 1, and each of $T_1$, $T_2$, $T_3$, $T_4$, and $\Delta H$ was obtained.

The results of the temperature analysis in ° C. of the microcapsules is reported below as per their temperature of full clearing (T4) and temperature of full colour return (T1) as well as practical hysteresis ΔH. The results are reported below for the Components C) with different $R_1$ groups as shown in the formula below.

| Example | T1 | T2 | T3 | T4 | ΔH |
|---|---|---|---|---|---|
| Example 1 | −20 | −5 | 55 | 71 | 60 |
| Example 2 | 4 | 18 | 60 | 78 | 42 |
| Example 3 | 30 | 40 | 75 | 87 | 35 |
| Example 4 | −20 | −15 | 55 | 71 | 70 |
| Example 5 | −25 | −10 | 43 | 70 | 53 |
| Example 6 | −18 | −10 | 45 | 70 | 55 |
| Example 7 | −20 | −10 | 40 | 67 | 50 |
| Example 8 | −15 | −10 | 55 | 73 | 65 |
| Example 9 | 2 | 19 | 45 | 72 | 26 |
| Example 10 | 20 | 27 | 55 | 82 | 28 |
| Example 11 | −20 | −15 | 35 | 60 | 50 |
| Example 12 | 18 | 21 | 55 | 65 | 34 |
| Example 13 | −3 | 2 | 45 | 60 | 43 |
| Example 14 | −20 | −16 | 45 | 65 | 61 |
| Example 15 | −23 | −20 | 34 | 38 | 54 |
| Example 16 | 15 | 25 | 55 | 65 | 30 |
| Example 17 | +2 | +8 | 40 | 52 | 32 |

The compositions produced in Examples 1 to 17 exhibited colour change characteristics and a hysteresis range were suitable for use as thermochromic compositions in temperature-indicator products according to the invention, for example as described in FIGS. 1 to 3.

The invention claimed is:

1. A temperature-indicator product comprising a visual indicator comprising a printed thermochromic colour-memory composition and comprising an electron-donating colouring organic compound (A), an electron-accepting colouring organic compound (B) and reaction medium compound (C), the said composition being printed on a substrate, wherein the visual indicator comprises a first portion comprising a first thermochromic colour-change composition in its lower temperature state that is coloured and a second portion comprising a second thermochromic colour-change composition in its higher temperature state that is colourless.

2. A temperature indicator product according to claim 1, in which the first thermochromic composition and the second thermochromic composition are the same composition.

3. A temperature indicator product according to claim 2, in which the first thermochromic composition has been subjected to a temperature not above its T2 temperature prior to application to the product and the second thermochromic portion has been subjected to a temperature not below its T3 temperature prior to application to the product.

4. A temperature indicator product according to claim 1, in which the first thermochromic composition and the second thermochromic composition are different compositions.

5. A temperature-indicator product comprising a visual indicator comprising a printed thermochromic colour-memory composition and comprising an electron-donating colouring organic compound (A), an electron-accepting colouring organic compound (B) and reaction medium compound (C), the said composition being printed on a substrate, wherein the visual indicator comprises a first portion comprising a first thermochromic colour-change composition and a second portion comprising an irreversible colour change ink, wherein the ink has a colour change temperature below the colour change temperature of the thermochromic composition.

6. A temperature indicator product according to claim 1 wherein the component C) comprises a compound of formula (I):

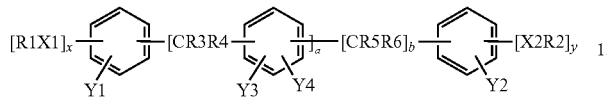

wherein:
R$_1$, and R$_2$ are independently selected from an optionally substituted linear or branched alkyl group, alkenyl group, alkoxy group, aryl group and an alkylene aryl group; having from 5 to 22 carbon atoms;

X$_1$ and X$_2$ are independently selected from —OC(O)—, —CO$_2$— and O;

R$_3$, R$_4$ and R$_5$ are independently selected from hydrogen and an optionally substituted linear or branched hydrocarbyl group;

R$_6$ is selected from hydrogen, halogen R$_3$, —X$_1$R$_1$, optionally substituted aryl;

Y$_1$, Y$_2$, Y$_3$ and Y$_4$ are independently selected from hydrogen, R$_3$, —OR$_3$ and halogen;

a is 0 to 4; b is 0 or 1; x and y are independently 0 or 1.

7. A temperature indicator product according to claim 1 adapted for use as a tamper-evident indicator.

8. A temperature indicator product according to claim 1 adapted for use as low temperature or freeze indicator.

9. A label comprising a temperature indicator product according to claim 1.

* * * * *